United States Patent [19]

Chia et al.

[11] 4,410,507

[45] Oct. 18, 1983

[54] PROCESS FOR THE PREPARATION OF PHYSIOLOGICALLY DEGRADABLE, COLLOIDAL RADIOISOTOPE CARRIERS AND THEIR USE

[75] Inventors: Han-Lie Chia, Reinach; Siegfried Woltmann, Magden, both of Switzerland

[73] Assignee: Solco Basel AG, Basel, Switzerland

[21] Appl. No.: 336,006

[22] Filed: Dec. 30, 1981

[30] Foreign Application Priority Data

Aug. 28, 1981 [CH] Switzerland .......................... 5560/81

[51] Int. Cl.³ ...................... A61K 43/00; A61K 49/00
[52] U.S. Cl. ..................................... 424/1.1; 252/311; 252/316; 252/301 R; 252/302; 128/650; 260/112 B; 260/112 R
[58] Field of Search ...................... 424/1, 1.5; 252/311

[56] References Cited

U.S. PATENT DOCUMENTS

| Re. 29,066 | 12/1976 | Evans | 424/1 |
|---|---|---|---|
| 3,803,299 | 4/1974 | Nonel | 424/1 |
| 3,863,004 | 1/1975 | Wolfangel | 424/1 |
| 3,872,226 | 3/1975 | Haney et al. | 424/1 |
| 4,024,233 | 5/1977 | Winchell et al. | 424/1 |
| 4,042,677 | 8/1977 | Molinski et al. | 424/1 |
| 4,094,965 | 6/1978 | Layne et al. | 424/1.5 |
| 4,187,285 | 2/1980 | Meeks et al. | 424/1 |
| 4,226,846 | 10/1980 | Saklad | 424/1 |
| 4,293,537 | 10/1981 | Wong | 424/1 |
| 4,305,922 | 12/1981 | Rhodes | 424/1 |

FOREIGN PATENT DOCUMENTS

| 1389809 | 4/1975 | United Kingdom . |
| 1409176 | 10/1975 | United Kingdom . |
| 2042887 | 1/1980 | United Kingdom . |

*Primary Examiner*—Brooks H. Hunt
*Assistant Examiner*—M. Moskowitz
*Attorney, Agent, or Firm*—Ladas & Parry

[57] ABSTRACT

A colloidal solution of human serum albumin is prepared by mixing an aqueous solution of the latter with a non-ionic surface-active agent and an acid solution of a tin(II) salt, adjusting the pH to 3.5 to 8.0 and heating at a constant temperature between 45° and 100° C. until complete hydrolysis of the tin(II) salt and denaturation of the albumin have taken place; the colloidal solution can also be lyophilized. By treating the solution or the lyophilizate with a $^{99m}$Tc-pertechnetate solution, a colloidal preparation is obtained for scintigraphy of the reticuloendothelial system or the lymphatic system. By suitable pH adjustment, the process makes it possible selectively to obtain colloids with a particle size of, for example, 3.0–0.2 or 0.2–0.03 or below 0.03 μm.

6 Claims, No Drawings

PROCESS FOR THE PREPARATION OF PHYSIOLOGICALLY DEGRADABLE, COLLOIDAL RADIOISOTOPE CARRIERS AND THEIR USE

Radioactively labeled colloidal particles have already been used in nuclear medicine for scintigraphic investigations, in particular for perfusion lung scintigraphy and also for investigations of the reticuloendothelial system. Technetium-99m is usually used as the radioisotope because of its particularly favorable radiological and physical properties ($T_{\frac{1}{2}}$ disintegration = 6.05 hours, gamma ray energy: 140 keV).

Various particulate materials have been proposed or used as carriers or matrices for the radioisotope, including proteins such as human serum albumin and hemoglobin [G. V. Taplin et al., J. Nucl. Med. 5 (1964), 259]. The use of human serum albumin (HSA) as the colloidal material is advantageous in many respects because HSA colloids or particles are well tolerated by humans and their ability to be metabolized has been unambiguously proved both by histological investigations on lung tissue and by radioactivity measurements.

To obtain products of reproducible particle size, various processes of preparation have been proposed, for example the coagulation of HSA in the presence of a tin(II) salt, in physiological saline solution (British Patent Specification No. 1,389,809), the denaturation of human protein by heat treatment at the isoelectric point of HSA (pH=4.9) and subsequent precipitation with dilute hydrochloric acid (British Patent Specification No. 1,409,176), the use of HSA after prior purification by dialysis (German Auslegeschrift No. 2,536,008), the specific use of tin(II) tartrate as a reducing agent (German Offenlegungsschrift No. 2,654,298), the mixing of metal ions in gelatine-HSA solution (U.S. Pat. No. Re. 29,066), or the use of buffer solutions (U.S. Pat. No. 4,024,233). With all these processes, however, mainly larger HSA particles with a particle size distribution from 10 to 100 μm were obtained; they are used for perfusion lung scintigraphy.

On the other hand, in the preparation of small colloidal HSA particles, complications arise as a result of aggregate formation, which is difficult to control. Because of their importance as a radioagnostic agent for the investigation of the reticuloendothelial system and the lymphatic system, attempts are therefore still being made to prepare small HSA particles with defined particle sizes.

Inter alia, the use of defatted human serum albumin as the starting material has been reported (German Offenlegungsschrift No. 2,814,038). HSA colloids with a particle size of 0.1–5 μm, predominantly for examination of the liver and spleen, or of 15–50 μm, for lung scintigraphy, were obtained therefrom. The preparation of HSA colloids with a particle size of 0.1–3.0 μm for the scintigraphic examination of reticuloendothelial systems, by the comminution of denatured HSA-Sn macroaggregates (10–100 μm) by means of ultrasound is known (U.S. Pat. No. 4,187,285). All these processes clearly require additional, expensive separation processes.

German Offenlegungsschrift No. 2,909,355 proposed a process for the preparation of HSA microaggregates with a particle size predominantly in the range 0.2–5 μm. In this process, the microaggregation of a mixture of human serum albumin and a tin(II) salt is effected by thermal denaturation, in particular in the presence of a ligand which stabilizes tin ions. The contribution of the ligand added before the microaggregation is essentially to enable a good radioactive examination of the reticuloendothelial system. Examples of stabilizing ligands which were used are sodium methylenediphosphonate (MDP), diethylenetriaminepentaacetic acid (DTPA), hydroxyethyldiphosphonate (HEDP), sodium pyrophosphate and disodium hydrogen phosphate. HSA microaggregates with a relatively broad particle size distribution, namely about 40 to 70% of the particles in the range 0.2–3 μm and about 10 to 30% in a range below 0.2 μm, were obtained by this process.

The colloidal preparations obtained by this process are only suitable for the scintigraphic examination of morphological damage to the reticuloendothelial system, in particular of the liver and the spleen (simultaneous examination of the liver and spleen), but they are only of limited use for the scintigraphic examination of bone marrow. As is known, a better examination of bone marrow is achieved with colloidal preparations of smaller particle size (predominantly below 0.2 μm).

Furthermore, these preparations have a broad and varying particle size distribution and are therefore unsuitable for investigations of the dynamic state or of the dynamic processes of the RE system.

Finally, they cannot be used for the scintigraphic examination of the lymphatic system, for which, as is known, colloidal preparations of smaller particle size are necessary. At the present time, the $^{99m}$Tc-antimony-sulfur colloid, which has a particle size of 0.002–0.015 μm but cannot easily be metabolized biologically [G. N. Ege et al., Brit. J. Radiol. 52 (1979), 124], is generally used for this purpose.

For the reasons mentioned, there is clearly still no radioactive colloidal preparation, at the present time,
1. which is suitable not only for morphological examination, but also, in particular, for functional scintigraphic examinations of the RE system,
2. which permits a good examination of bone marrow, and
3. which possesses better properties for the scintigraphic examination of the lymphatic system than the $^{99m}$Tc-antimony-sulfur colloids or $^{99m}$Tc-sulfur colloids available at the present time.

For a quantitative functional test for the RE system, a colloidal product having the following properties is required (I. Zolle et al., Radioaktive Isotopen in Klinik und Forschung [Radioactive Isotopes in Hospitals and Research], Gasteiner Symposium 1972, Volume 10, page 446):
1. smaller particles with an exactly defined, homogeneous or narrower particle size distribution,
2. good reproducibility from one preparation to the next,
3. good labeling stability and
4. good tolerance and ability to be metabolized in humans.

For the scintigraphic examination of the RE cells of bone marrow, it is desired to have a colloidal product which, in addition to the abovementioned properties, has a particle size in a range below 0.2 μm. As is known, there is a relationship between particle size and degree of concentration of the colloids in the bone marrow. Better concentration in the bone marrow is achieved with smaller particles [H. L. Atkins et al., J. of Reticuloendothelial Soc. 8 (1970), 176] and their particle size is generally accepted as ideal in the range from 0.03–0.2 μm.

An ideal colloidal preparation for the scintigraphic examination of the lymphatic system should have the following properties [G. N. Ege et al., Brit. J. Radiol. 52 (1979), 124]:
1. a homogeneous particle size distribution defined as narrowly as possible; it is accepted that the optimum particle size should be in the range from 0.002–0.03 μm;
2. a stable preparation; an agglomeration process should not take place;
3. good reproducibility from one preparation to the next;
4. good ability to be labeled by the radioisotope, which should have favorable physical and radiological properties;
5. good tolerance and ability to be metabolized in humans; and
6. the preparation should have the smallest possible residual activity at the site of injection after subcutaneous administration.

A process has now been found for obtaining preparations which can be labeled with technetium-99m and contain colloidal human serum albumin, and which have the abovementioned properties and, after labeling with technetium-99m, are thus outstandingly suitable not only for morphological and, as well, functional scintigraphic investigations of the RE system (of the liver, of the spleen and even of bone marrow) but also for the examination of the lymphatic system.

By means of the process according to the invention, it is possible
1. to obtain colloidal preparations of smaller particle size, the particle size range of which can be specifically controlled according to the proposed use,
2. to keep the particle size distribution of the colloidal preparations obtained therefrom particularly narrow and defined,
3. to produce reproducible products with a defined particle size distribution from one preparation to the next,
4. specifically to obtain colloidal preparations with a narrow and defined particle size distribution in a range below 3.0 μm, according to the proposed use, such as, for example, in the range from 0.2–3.0 μm, from 0.03–0.2 μm and below 0.03 μm, and
5. to obtain, with the same principle of preparation, at least two new colloidal preparations, namely preparations for the scintigraphic examination of the liver and spleen, for functional scintigraphic examinations of the RE system and for the scintigraphic examinations of bone marrow and of the lymphatic system.

The process according to the invention is based on the finding that, with the concentrations of the components kept constant, the particle size and the particle size distribution of the colloidal product formed are dependent solely on the pH value of the mixture before microaggregation. The components are human serum albumin, tin(II) ions and non-ionic surface-active agents in a buffer solution. It has been shown that the particle size range of the colloidal product formed can be controlled exactly by accurate pH adjustment before microaggregation. Surprisingly, it has been established that the particle size distribution of the colloidal product formed therefrom is narrowly defined and reproducible. This, however, requires leaving out the ligand which, according to already mentioned German Offenlegungsschrift No. 2,909,355, should be used before microaggregation. While with said earlier method the pH value in any case has to be adjusted according to the particular ligand used, adjusting the pH value alone has been found to bring about at once the above mentioned results.

The process according to the invention comprises mixing the above mentioned components, adjusting the reaction mixture to a constant pH value preselected in the range from 3.5 to 8.0 by adding a buffer solution, and heating the mixture at a constant temperature in the range from 45° to 100° C. by means of a microwave oven or whilst stirring until hydrolysis of the tin(II) salt and denaturation of the human serum albumin have been achieved.

Heating by means of a microwave oven has the advantage that the complete hydrolysis, together with simultaneous denaturation of the albumin, takes place homogeneously because of the uniform heat supply.

The invention is described in detail below.

Any commercial product can be used as human serum albumin without special purification or pretreatment and especially without prior defatting or purification by dialysis, ultrafiltration or column chromatography. An aqueous solution is prepared therefrom, the concentration of which is advantageously 0.05 to 20 mg/ml, preferably 0.2 to 2.5 mg/ml.

For the freeze-drying of the colloidal material, which follows the preparation if desired, it has proved advantageous to add, to the solution obtained, a pharmacologically inert filler and a substance acting as a stabilizer. As a result of these additions, the freeze-drying leads to a qualitatively better lyophilizate.

During the labeling with $^{99m}$Tc-sodium pertechnetate in physiologically saline solution, the product can therefore be dissolved more easily and it remains as a stable colloid at the physiological pH value. An aqueous solution of 0.05 to 40 mg of dextrose and 0.01 to 5 mg of sodium inositolhexaphosphate (sodium phytate) per ml, preferably of 10 to 20 mg of dextrose and 0.1 to 0.5 mg of sodium phytate per ml, is suitable, in particular, for these additions.

Apart from the abovementioned substances, it is of course possible to use other substances acting as fillers or stabilizers, for example carbohydrate derivatives (mannitol, fructose, lactose, inositol and sorbitol), glycine, sodium chloride, human serum albumin, inorganic phosphates, sulfates and carbonates, monocarboxylic acids, phosphonates and the like. Detailed articles on this subject can be found in the following monographs: H. Sucker, P. Fuchs and P. Speiser, editors: Pharmazeutische Technologie [Pharmaceutical Technology], pages 321–332 and 620–628, Georg Thieme Verlag, Stuttgart 1978; P. H. List and L. Hörhammer, editors: Hagers Handbuch der pharmazeutischen Praxis [Hager's Handbook of Pharmaceutical Practice], Volume 7, pages 297–302, 4th edition, Springer-Verlag, Berlin 1971.

If appropriate, the solubility of the lyophilized product can also be improved by keeping the material at a constant temperature between 35° and 75° C., for 1 to 3 hours, before lyophilization. The colloidal particles already formed are thereby also stabilized with reducing action, and their good solubility or resuspendability is maintained.

The surface-active agents used are water-soluble, non-ionic, non-toxic substances which are well tolerated on parenteral administration. As is known, these substances are designated as solubilizers, wetting agents, emulsifiers, surface-active agents, detergents or solubilizing agents, depending on the proposed use. Accordingly, the following substances, inter alia, can be used: Tween 80, Carbowax or polyethylene glycols type 600, 1,500 or 4,000, poly-N-vinylpyrrolidone type 20 or 40, Plasdone type C-15, polysaccharide derivatives such as dextran, protein derivatives such as gelatine, and propylene oxide/ethylene oxide block polymers (Pluriol-PE or Pluronics type F-38, F-88, F-98 or F-108, Cremophors type EL, RH-40 and RH-60, and Tergitols). Detailed examples of these classes of substances can be found in the following monograph: H. P. Fiedler and H. v. Czetsch-Lindenwald: Lexikon der Hilfsstoffe für Pharmazie, Kosmetik und angrenzende Gebiete [Dictionary of Auxiliaries for Pharmacy, Cosmetics and Related Fields], Editio Cantor KG, Aulendorf i. Württemberg 1971.

The concentration of surface-active agent in the aqueous solution should generally be 1 to 20 times the concentration of HSA; preferably, 0.2 to 40 mg/ml of Pluronic F-88 are used.

The use of buffer solutions for strictly maintaining the predetermined pH value of the mixture before microaggregation has proved advantageous. Inter alia, the following can be used as buffers: sodium bicarbonate/sodium carbonate, borax/sodium hydroxide solution, dihydrogen phosphate (for example $NaH_2PO_4$)/monohydrogen phosphate (for example $Na_2HPO_4$)/phosphate (for example $Na_3PO_4$), potassium diphthalate/sodium hydroxide solution, sodium acetate, tris-(hydroxymethyl)-aminomethane (Tris buffer), 2-[4-(2-hydroxyethyl)-piperazin-1-yl]-ethanesulfonic acid/sodium hydroxide solution (HEPES buffer), and the like. Possible buffer systems have been collated in the following monographs: H. M. Rauen, editor: Biochemisches Taschenbuch [Biochemistry Pocketbook], 2nd edition, Volume 2, pages 90-104, Springer Verlag, Berlin 1964; N. E. Good, G. D. Winget, W. Winter, T. N. Conolly, S. Izawa and R. M. M. Singh, Biochemistry 5, 467 (1966); H. Eagle, Science 174, 500 (1971).

For reasons of simplicity, the aqueous solution, consisting of human serum albumin, a non-ionic surface-active agent and a tin(II) salt in hydrochloric acid, can first be mixed with the buffer solution, and the predetermined pH value can then be adjusted exactly with sodium hydroxide solution or hydrochloric acid.

The tin(II) salt can be, for example, $SnCl_2.2H_2O$, another tin(II) halide or tin(II) tartrate.

The pH value of the mixture before microaggregation is adjusted to between 3.0 and 8.0, depending on the desired particle size. If the buffer solution is not mixed immediately with the aqueous solution of human serum albumin, non-ionic surface-active agent and tin(II) ions in hydrochloric acid, the predetermined pH adjustment can be effected by means of an aqueous solution of buffer reagent and alkaline reagent, for example sodium hydroxide solution, potassium hydroxide solution, aqueous ammonia or an organic base. A buffer mixture which maintains the desired constant pH value before microaggregation is thereby formed in every case. The amount of buffer solution thus formed, or added, is advantageously such that its concentration in the solution is 0.05 to 50 mg/ml.

The pH is preferably adjusted within the range 5.8-6.8 for obtaining colloidal preparations with a particle size of 0.2-3.0 $\mu$m, but, on the other hand, it is preferably adjusted within the pH ranges 3.0-5.0 or 6.8-8.0 for the particle size 0.03-0.2 $\mu$m. These pH values apply, in particular, when the concentration of human serum albumin is 1.0-3.0 mg/ml, the concentration of surface-active agent is 1.0-40 mg/ml and the concentration of tin(II) salt is 0.1-0.8 mg of $SnCl_2.2H_2O$/ml. In the pH range from 6.0-6.8, a colloidal preparation with a particle size of 0.03-0.2 $\mu$m can be prepared, and in the range from 6.8-7.5, a colloidal preparation with a particle size below 0.03 $\mu$m can be prepared, when the concentration of human serum albumin is 0.2-1.2 mg/ml, the concentration of tin(II) salt is 0.05-0.4 mg of $SnCl_2.2H_2O$/ml and the concentration of surface-active agent is 1.0-40 mg/ml.

The hydrolysis of the tin(II) ions present in the reaction mixture already begins during the adjustment of the predetermined pH value by the buffer solution, the complete hydrolysis taking place simultaneously with the complete microaggregation process on heating the solution. As is known, the hydrolysis of the Sn(II) ions takes place in steps. Very probably, the heat treatment of the solution causes not only the complete microaggregation of the serum albumin, but also the dehydration of tin hydroxides to give sparingly soluble products which are present as colloidal particles, in combination with coagulated serum albumin.

The heat treatment is advantageously carried out by means of a microwave oven or by heating at constant temperature, whilst stirring. In this process, it is important that the chosen pH value is strictly maintained, the concentration ratios of the reaction components being kept constant. In general, the solution is kept at a specific temperature from 45°-100° C. As is known, the duration of the microaggregation process depends on the chosen temperature and on the volume; it can vary between 2 minutes and 2 hours and it generally remains within a range of 5-45 minutes. A shorter microaggregation time is achieved by heat treatment by means of a microwave oven at 100°-250° C. (50 seconds to 30 minutes). It has also been shown that the microaggregation of the products to be prepared can also be effected by circulating the solution in a continuous serpentine tube as the reaction vessel, in a heating bath. The flow is maintained by means of a delivery pump attached to the reaction circuit, the temperature of the heating bath advantageously being kept between 70°-90° C.

The resulting colloidal material can then be used direct for $^{99m}Tc$ labeling or freeze-dried and stored in this form up to the time of labeling with $^{99m}Tc$-sodium pertechnetate.

To facilitate the redissolution of the lyophilized product before labeling, it has proved advantageous to add to the material, before lyophilization, substances acting as fillers and stabilizers. A mixture of dextrose and sodium phytate (sodium inositolhexaphosphate) is preferred for this purpose because the outstanding properties of the pharmacologically acceptable dextrose and also the advantages of the high specific charge of sodium phytate (6 negative charges per molecule) are known. As a result, the colloidal particles already formed are better stabilized with reducing action, and their good solubility or resuspendability is retained.

A particularly preferred embodiment of the process consists in using Pluronic F-88 or Cremophor-EL as the non-ionic surface-active agent, disodium hydrogen phosphate or tris-(hydroxymethyl)-aminomethane (Tris buffer) or 2-[4-(2-hydroxyethyl)-piperazin-1-yl]-ethanesulfonic acid/sodium hydroxide solution (HEPES buffer) as the buffer and dextrose and sodium phytate as the filler and stabilizer respectively, the microaggregation being effected by means of a microwave oven.

Starting from the material prepared according to the invention (as a colloidal solution or in lyophilized form), a corresponding colloidal radioactive solution for scintigraphic investigations can easily be prepared by treating the material with a $^{99m}$Tc-pertechnetate solution, preferably an Na$^{99m}$TcO$_4$ solution.

It is clearly apparent from the analysis data given (Tables 1 and 2) that the present colloidal product is not merely a mixture of separately existing human serum albumin, tin(II)salt and other components which, as such, can be labeled separately with technetium-99m.

A mixture prepared without microaggregation (Product No. 4) behaves differently from the preparations according to the invention (Products No. 1, No. 2 and No. 3), as regards both the particle size distribution and the biological distribution after $^{99m}$Tc labeling. The mixture (Product No. 4) behaves like a water-soluble HSA reagent kit for blood volume examination (Product No. 5, commercial preparation). On the other hand, a true colloidal preparation (Products Nos. 1 to 3) is obtained by the process according to the invention. The difference between preparations No. 1, No. 2 and No. 3 according to the invention is that Product No. 1 has been prepared specifically with a particle size from 0.2–3.0 μm, Product No. 2 has been prepared with a particle size from 0.03–0.2 μm and Product No. 3 has been prepaed with a particle size below 0.03 μm. The particle size distribution is determined by means of microfiltration through Nucleopore filters, the smallest obtainable pore sizes of which are 0.03 μm. The fact that Product No. 3 according to the invention (particle size below 0.03 μm) is present in true colloidal form can be seen from its biological distribution (Table 2). After intravenous injection, a colloid is stored in the RE system by phagocytosis. By way of a summary, the data for the commercially available reagent kits (HSA colloids and Sb-S colloids), and also by way of comparison, the data for the $^{99m}$Tc-pertechnetate solution, are listed.

To determine the particle size, the $^{99m}$Tc-labeled product is passed through microfilters of defined pore size (Nucleopore filters). The activity of the solution before and after filtration is measured in a gamma counter and the particle size distribution is determined on the basis of the measured activity distribution.

For biodistribution, the $^{99m}$Tc-labeled product is administered intravenously into the caudal vein. 30 minutes after administration, the animals are sacrificed under ether narcosis and dissected, and the activity in the individual organs is measured in the gamma counter.

The biodata for rats, 2 hours after subcutaneous injection into the heel of the right hind leg, are listed in Table 3. Products Nos. 8 to 11 according to the invention are clearly suitable, inter alia, for the examination of the lymphatic system.

The labeling yield of the products is always above 95% according to radiochromatographic investigation. To determine the labeling yield, the $^{99m}$Tc-labeled preparations are radiochromatographed and the radiochromatogram is evaluated using a thin layer scanner. The absence of unbound $^{99m}$Tc-pertechnetate can be determined, inter alia, with the test systems listed in Table 4.

To prepare colloidal products for parenteral administration, it is necessary that the reagents, solutions and utensils to be used should be sterile and pyrogen-free and that all preparations and operational procedures should be carried out under a nitrogen atmosphere and aseptic conditions. The test for sterility is carried out according to U.S. Pharmacopeia XIX and the test for the absence of pyrogenic substances is carried out according to the European Pharmacopoeia.

EXAMPLE 1

Buffer solution: 1.0 mg of NaHCO$_3$ + 0.5 mg of NaOH/ml of water

In a closed 100 ml reaction vessel, 250 mg of human serum albumin (corresponding to 1.25 ml of 20% strength HSA solution) and 250 mg of dextrose are initially introduced into 70 to 75 ml of water. After the addition of 2.5 ml of 0.8% strength SnCl$_2$ solution in 0.1 N HCl, the mixture is adjusted to pH 6.37 with the buffer solution (amount used: 14.0 ml). The weakly opalescent mixture is diluted with water to a volume of 90 ml and heated at 80° C. for 3 minutes. The milky suspension is cooled to room temperature and warmed again at 60° C. for 60 minutes. Before lyophilization, 10 ml of a solution of soluble HSA and Na$_2$HPO$_4$ (corresponding respectively to 100 mg of HSA and of Na$_2$HPO$_4$ per ml) are added and the resulting solution is lyophilized in ampoules of 1 ml capacity.

1 ampoule contains:
  2.5 mg of HSA in colloidal form
  0.2 mg of SnCl$_2$.2H$_2$O
  2.5 mg of dextrose
  10.0 mg of soluble HSA as a filler
  10.0 mg of Na$_2$HPO$_4$ as a stabilizer
  NaHCO$_3$/NaOH as a buffer before microaggregation.

The biodata for the $^{99m}$Tc-labeled product are listed in Table 5.

EXAMPLE 2

Buffer solution:
  1.0 mg of NaHCO$_3$ + 0.5 mg of NaOH/ml of water
  The procedure of Example 1 is followed; pH adjustment to 6.98.

1 ampoule contains:
  0.5 mg of HSA in colloidal form
  0.2 mg of SnCl$_2$.2H$_2$O
  2.0 mg of Cremophor RH-40
  10.0 mg of soluble HSA as a filler
  10.0 mg of Na$_2$HPO$_4$ as a stabilizer
  NaHCO$_3$/NaOH as a buffer before microaggregation.

See Table 5 for biodata.

EXAMPLE 3

Buffer solution:
  1.0 mg of disodium tetraborate + 0.5 mg of NaOH/ml of water 250 mg each of human serum albumin and polyvinylpyrrolidone (KW 29-32) are initially introduced into 50 ml of water. 2.5 ml of 0.8% strength solution of SnCl$_2$.2H$_2$O in 0.1 N hydrochloric acid are added. The pH value of the weakly opalescent solution is adjusted to 6.5 with the buffer solution (amount used: 15 ml). After the addition of water to a volume of 95 ml, the solution is heated at 80° C. for 3 minutes. The subsequent treatment is performed as in Example 1.

1 ampoule contains:
  2.5 mg of HSA in colloidal form
  0.2 mg of SnCl$_2$.2H$_2$O
  2.0 mg of polyvinylpyrrolidone 10.0 mg of soluble HSA as a filler
10.0 mg of Na$_2$HPO$_4$ as a stabilizer
borax/NaOH as a buffer before microaggregation.
See Table 5 for biodata.

EXAMPLE 4

Buffer solution:
11.92 mg of 2-[4-(2-hydroxyethyl)piperazin-1-yl]-ethanesulfonic acid (HEPES)+2.0 mg of sodium hydroxide/ml of H$_2$O In a closed 100 ml vessel, 250 mg each of HSA and Cremophor-EL are dissolved in 50 to 60 ml of water. 2.5 ml of 0.8% strength solution of SnCl$_2$.2H$_2$O in 0.1 N HCl are added. The pH value is adjusted to 6.4 by adding the buffer solution. The weakly opalescent solution is heated for 60 seconds in a microwave oven (output power: 1,500 watts). 1.5 g of dextrose and 250 mg of anhydrous sodium phytate are added to the milky solution. The colloidal solution is lyophilized in ampoules of 1 ml capacity.
See Table 5 for biodata.

EXAMPLE 5

Buffer solution:
Na$_2$HPO$_4$/NaOH

In a closed 100 ml reaction vessel, the following are dissolved successively in 50 to 60 ml of water: 250 mg each of HSA and Pluronic F-88, 2.5 ml of 1.6% strength SnCl$_2$.2H$_2$O in 0.1 N HCl and 50 mg of Na$_2$HPO$_4$. The pH is adjusted to 6.4 by adding 0.025 N NaOH. The weakly opalescent mixture is worked up further as in Example 4 and lyophilized.
See Table 5 for biodata.

EXAMPLE 6

Buffer solution:
1.0 mg of disodium tetraborate+0.5 mg of NaOH/ml of water

In a closed 100 ml reaction vessel, 50 mg of HSA, 200 mg of Pluronic F-68 and 20.0 mg of SnCl$_2$.2H$_2$O in 0.1 N HCl are mixed in 50 to 60 ml of water. The pH of the mixture is adjusted to 6.9 with the buffer solution and the mixture is then diluted to 100 ml with water. The weakly opalescent mixture is heated by means of a microwave oven as in Example 4. The colloidal solution is labeled with $^{99m}$Tc-pertechnetate.
See Table 5 for biodata.

EXAMPLE 7

Buffer solution:
5.0 mg of Na$_2$HPO$_4$ and 1.0 mg of NaOH/ml of water
The procedure of Example 6 is followed: pH adjustment to 6.8.
1 ampoule contains:
0.5 mg of HSA in colloidal form
0.2 mg of SnCl$_2$.2H$_2$O
2.0 mg of Cremophor-EL
15.0 mg of dextrose
0.25 mg of anhydrous sodium phytate
Na$_2$HPO$_4$/NaOH as a buffer before microaggregation.
See Table 5 for biodata.

TABLE 1

Microfiltration of the $^{99m}$Tc-labeled products through Nucleopore filters
% distribution of the particle size

| Product No. 1 | 2 | 3 | 4 | 5 | 6 | 7 | for comparison |
|---|---|---|---|---|---|---|---|
| Colloid according to the process | Colloid according to the process | Colloid according to the process | Mixture according to the process, before the microaggregation | Commercial soluble HSA reagent kit | Commercial HSA colloid | Commercial Sb-S colloid | $^{99m}$TcO$_4^-$ from the generator |
| >3 μm: 0% <br> 3 to 0.2 μm: 96.7% <br> <0.2 μm: 3.3% | >0.2 μm: 0% <br> 0.2 to 0.03 μm: 100% | >0.2 μm: 4.5% <br> 0.1 to 0.03 μm: 3.5% <br> <0.03 μm: 92.5% | 1 to 0.1 μm: 0% <br> <0.2 μm: 100% | 3 to 0.2 μm: 0% <br> <0.2 μm: 98% | >5 μm: 7.0% <br> 5 to 3 μm: 21.0% <br> 3 to 0.2 μm: 68.0% <br> <0.2 μm: 3.5% | >0.2 μm: 0.7% <br> <0.2 μm: 99.3% | >0.2 μm: 2% <br> <0.2 μm: 98% |

TABLE 2

Biodistribution of the $^{99m}$Tc-labeled preparations (30 minutes after intravenous administration) % administered dose, average of 3 animals

| Product No. 1 | 1 | 2 | 3 | 4 | 5 | 6 | 7 | for comparison |
|---|---|---|---|---|---|---|---|---|
| Preparation | Colloid according to the process | Colloid according to the process | Colloid according to the process | Mixture according to the process but before the microaggregation | Commercial soluble HSA reagent kit | Commercial HSA colloid | Commercial Sb-S colloid | $^{99m}$TcO$_4^-$ from the generator |
| Particle size (mainly in the range) | 0.2–3.0 μm | 0.03–0.02 μm | smaller than 0.03 μm | smaller than 0.2 μm | smaller than 0.2 μm | broad distribution (see Table 1) 0.2–0.3 μm | smaller than 0.2 μm | smaller than 0.2 μm |
| Biodata | Rats | Rats | Mice | Rats | Mice | Mice | Mice | Mice |
| Blood | 0.37 | 0.59 | 2.63 | 14.86 | 28.5 | 1.06 | 13.3 | 8.0 |
| Lungs | 0.19 | 0.18 | 0.27 | 0.78 | 2.1 | 6.15 | 1.9 | 1.2 |

TABLE 2-continued

Biodistribution of the $^{99m}$Tc-labeled preparations (30 minutes after intravenous administration) % administered dose, average of 3 animals

| Product No. | 1 | 2 | 3 | 4 | 5 | 6 | 7 | for comparison |
|---|---|---|---|---|---|---|---|---|
| Preparation | Colloid according to the process | Colloid according to the process | Colloid according to the process | Mixture according to the process but before the micro-aggregation | Commercial soluble HSA reagent kit | Commercial HSA colloid | Commercial Sb-S colloid | $^{99m}$TcO$_4^-$ from the generator |
| Liver | 81.48 | 78.78 | 80.04 | 29.87 | 15.7 | 78.78 | 66.5 | 6.8 |
| Spleen | 2.20 | 1.45 | 1.76 | 0.55 | 0.5 | 1.58 | 1.2 | 0.3 |
| Kidneys | 0.69 | 5.33 | 1.63 | 10.52 | 4.9 | 0.98 | 1.3 | 1.2 |
| Stomach + Intestinal tract | 0.20 | 1.74 | 1.30 | 3.39 | 7.7 | 2.12 | 2.7 | 39.5 |
| Bones and bone marrow | 6.07 | 8.89 | 10.10 | 14.64 | 27.9 | 2.66 | 9.1 | 5.0 |
| Muscles | 0.62 | 2.59 | 1.54 | 8.24 | 0.1 | 1.32 | 0.1 | 0.0 |
| Urine | 0.49 | 3.00 | 2.26 | 13.09 | 12.4 | 2.23 | 4.9 | 11.4 |

TABLE 3

Biodistribution in rats 2 hours after subcutaneous administration % administered dose, average of 2 animals

| Product No. | 8 | 9 | 10 | 11 | 5 | 7 | 12 | for comparison |
|---|---|---|---|---|---|---|---|---|
| Origin | According to the process | According to the process | According to the process | According to the process | Commercial | Commercial | Commercial | $^{99m}$TcO$_4^-$ from the generator |
| Note | HSA colloid Sn reducing agent Cremophor NaHCO$_3$/NaOH buffer | HSA colloid Sn reducing agent Pluronic borax/NaOH buffer | HSA colloid Sn reducing agent Cremophor Na$_2$HPO$_4$/NaOH buffer | HSA colloid Sn reducing agent Pluronic Na$_2$HPO$_4$/NaOH buffer | soluble HSA-Sn reagent kit for blood volume | Sb-S colloid for lymphatic system | sulfur colloid for lymphatic system | free $^{99m}$Tc-pertechnetate |
| Site of injection (right heel) | 47.7 | 56.46 | 56.58 | 51.20 | 63.91 | 52.66 | 71.95 | 3.40 |
| Popliteal lymph node | | | | | | | | |
| right | 12.0 | 13.39 | 14.46 | 17.15 | 1.57 | 7.88 | 6.12 | 0.03 |
| left | 0.006 | 0.007 | 0.005 | 0.002 | 0.001 | 0.002 | 0.0 | 0.01 |
| Inguinal lymph node | | | | | | | | |
| right | 0.02 | 0.02 | 0.006 | 0.003 | 0.026 | 0.005 | 0.0 | 0.01 |
| left | 0.01 | 0.003 | 0.006 | 0.003 | 0.026 | 0.005 | 0.0 | 0.01 |
| Ext. iliac lymph node | | | | | | | | |
| right | 2.12 | 1.00 | 6.51 | 6.22 | 1.11 | 5.86 | 2.31 | 0.01 |
| left | 0.10 | 0.002 | 0.003 | 0.02 | 0.04 | 0.002 | 0.0 | 0.00 |
| Renal lymph node | | | | | | | | |
| right + left | 0.006 | 0.001 | 0.004 | 0.002 | 0.14 | 0.002 | 0.0 | 0.01 |
| Blood | 7.41 | 1.09 | 2.82 | 1.20 | 5.98 | 3.45 | 1.35 | 8.65 |
| Liver | 2.74 | 0.35 | 2.28 | 1.22 | 1.78 | 2.93 | 2.26 | 3.48 |
| Spleen | 0.08 | 0.01 | 0.09 | 0.04 | 0.23 | 0.38 | 0.03 | 0.10 |
| Kidneys | 4.20 | 1.88 | 3.42 | 1.71 | 3.79 | 0.99 | 0.92 | 1.52 |

TABLE 4

Radiochromatographic test systems for $^{99m}$Tc colloids

| Rf values | Merck silica gel pre-coated plate 0.9% strength sodium chloride solution | Whatman-ET 31 acetone |
|---|---|---|
| Free pertechnetate | 1.0 | 1.0 |
| Bound radio-isotope | 0.0 | 0.0 |

TABLE 5

Summary of the examples of the patent Biodata 30 minutes after intravenous administration
Average of 3 animals

| Example No. 1 | 1 | 2 | 3 | 4 | 5 | 6 | 7 | 8 |
|---|---|---|---|---|---|---|---|---|
| Colloid | HSA | HSA | HSA | HSA | HSA | HSA | HSA | HSA |
| Reducing agent | $SnCl_2.2H_2O$ | $SnCl_2.2H_2O$ | $SnCl_2.2H_2O$ | $SnCl_2.2H_2O$ | $SnCl_2.2H_2O$ | $SnCl_2.2H_2O$ | $SnCl_2.2H_2O$ | $SnCl_2.2H_2O$ |
| Wetting agent | Dextrose | Cremophor RH-40 | Polyvinyl-pyrrolidone | Cremophor EL | Pluronic F-88 | Pluronic F-68 | Cremophor EL | Pluronic F-68 |
| Buffer | $NaHCO_3$ + NaOH | $Na_2HPO_4$ + NaOH | Na tetra-borate + NaOH | HEPES + NaOH | $Na_2HPO_4$ + NaOH | Na tetra-borate + NaOH | $Na_2HPO_4$ + NaOH | Citric acid + NaOH |
| pH before heating | 6.4 | 6.1 | 6.5 | 6.4 | 6.4 | 6.9 | 6.8 | 5.9 |
| Filler | Soluble HSA | Soluble HSA | Soluble HSA | Dextrose | Dextrose | — | Dextrose | Soluble HSA |
| Stabilizer | $Na_2HPO_4$ | $Na_2HPO_4$ | $Na_2HPO_4$ | Na phytate | Na phytate | — | Na phytate | $Na_2HPO_4$ |
| % Administered dose | (Mice) | (Mice) | (Mice) | (Mice) | (Mice) | (Mice) | (Mice) | (Mice) |
| Blood | 2.78 | 3.10 | 3.41 | 1.61 | 1.18 | 1.10 | 1.82 | 4.36 |
| Lungs | 0.36 | 0.54 | 0.32 | 0.37 | 0.94 | 0.17 | 0.73 | 0.52 |
| Liver | 67.35 | 76.45 | 74.84 | 80.81 | 80.81 | 77.72 | 82.21 | 72.17 |
| Spleen | 0.78 | 0.67 | 0.63 | 1.32 | 1.36 | 1.27 | 1.19 | 1.19 |
| Kidneys | 6.04 | 1.83 | 3.00 | 0.96 | 0.62 | 0.61 | 1.56 | 1.91 |
| Stomach + intestinal tract | 3.62 | 2.27 | 3.65 | 1.07 | 1.12 | 1.29 | 0.85 | 2.34 |
| Bones and bone marrow | 5.65 | 4.80 | 6.02 | 4.81 | 3.18 | 7.90 | ? | 5.00 |
| Muscles | 1.63 | 1.15 | 1.72 | 1.24 | 0.96 | 0.78 | 1.98 | 0.90 |
| Urine | 4.44 | 2.38 | 2.16 | 0.33 | 1.50 | ? | ? | 2.00 |

EXAMPLE 8

Buffer solution:
5.0 mg of citric acid monohydrate + 1.0 mg of sodium hydroxide/ml of water The procedure of Example 6 is followed; pH adjustment to 5.9.

1 ampoule contains:
0.5 mg of HSA in colloidal form
0.2 mg of $SnCl_2.2H_2O$
2.0 mg of Pluronic F-68
10.0 mg of HSA as a filler
10.0 mg of $Na_2HPO_4$ as a stabilizer
Citric acid + NaOH as a buffer before microaggregation.

See Table 5 for biodata.

We claim:

1. A process for the preparation of a physiologically degradable, colloidal material which can be labeled with technetium-99m and contains human serum albumin, and which is of small particle size and narrow and defined particle size distribution, which comprises mixing an aqueous solution of human serum albumin with a non-ionic surface-active agent and an aqueous acid solution of a tin(II) salt in the absence of ligands for the tin(II) salt, adjusting the pH value of the reaction mixture to a constant preselected pH value of 3.0 to 8.0 by the addition of a buffer solution, and heating the mixture at a constant temperature in the range from 45° to 100° C., by the action of microwaves or whilst stirring, until complete hydrolysis of the tin(II) salt and simultaneous denaturation of the human serum albumin have taken place.

2. A process as claimed in claim 1, wherein an aqueous solution of tin(II) chloride in hydrochloric acid is used as the aqueous acid solution of a tin(II) salt.

3. A process as claimed in claim 1 or 2, wherein the colloidal solution obtained is freeze-dried.

4. A process as claimed in claim 3, wherein dextrose and sodium inositolhexaphosphate (sodium phytate) are added to the colloidal solution before freeze-drying.

5. A process for the preparation of a physiologically degradable, colloidal material which is labeled with technetium-99m, contains human serum albumin and is of small particle size and narrow and defined particle size distribution, which comprises mixing an aqueous solution of human serum albumin with a non-ionic surface-active agent and an aqueous acid solution of a tin(II) salt in the absence of ligands for the tin(II) salt, adjusting the pH values of the reaction mixture to a constant preselected pH value of 3.0 to 8.0 by the addition of a buffer solution, heating the mixture at a constant temperature in the range from 45° to 100° C. by the action of microwaves or whilst stirring until complete hydrolysis of the tin(II) salt and simultaneous denaturation of the human serum albumin have taken place, and treating the formed colloidal material with a solution of technetium-99m.

6. A process according to claim 9 wherein said formed colloidal material is freeze-dried before treatment with said solution of technetium-99m.

* * * * *